(12) United States Patent
Kidoaki et al.

(10) Patent No.: US 10,316,292 B2
(45) Date of Patent: Jun. 11, 2019

(54) MATERIAL FOR UNDIFFERENTIATED STATE-MAINTAINING CULTURE

(71) Applicants: NISSAN CHEMICAL INDUSTRIES, LTD., Tokyo (JP); KYUSHU UNIVERSITY, Fukuoka-shi, Fukuoka (JP)

(72) Inventors: Satoru Kidoaki, Fukuoka (JP); Yukie Tuji, Fukuoka (JP); Hisato Hayashi, Funabashi (JP); Takehisa Iwama, Funabashi (JP); Masato Horikawa, Chiyoda-ku (JP)

(73) Assignees: NISSAN CHEMICAL INDUSTRIES, LTD., Tokyo (JP); KYUSHU UNIVERSITY, Fukuoka (JP)

( * ) Notice: Subject to any disclaimer, the term of this patent is extended or adjusted under 35 U.S.C. 154(b) by 0 days.

(21) Appl. No.: 15/113,628

(22) PCT Filed: Jan. 23, 2015

(86) PCT No.: PCT/JP2015/051929
§ 371 (c)(1),
(2) Date: Jul. 22, 2016

(87) PCT Pub. No.: WO2015/111734
PCT Pub. Date: Jul. 30, 2015

(65) Prior Publication Data
US 2017/0009209 A1    Jan. 12, 2017

(30) Foreign Application Priority Data
Jan. 23, 2014  (JP) .................. 2014-010593

(51) Int. Cl.
*C12N 5/0775*    (2010.01)
*C12N 5/00*    (2006.01)
*B82Y 30/00*    (2011.01)

(52) U.S. Cl.
CPC ......... *C12N 5/0668* (2013.01); *C12N 5/0018* (2013.01); *C12N 5/0663* (2013.01); *B82Y 30/00* (2013.01); *C12N 2500/34* (2013.01)

(58) Field of Classification Search
None
See application file for complete search history.

(56) References Cited

U.S. PATENT DOCUMENTS

| 2004/0043434 | A1 | 3/2004 | Feng |
| 2007/0148767 | A1 | 6/2007 | Yang et al. |
| 2010/0233234 | A1 | 9/2010 | Arinzeh et al. |

FOREIGN PATENT DOCUMENTS

| JP | 2008-541728 A | 11/2008 |
| JP | 2009-065854 A | 4/2009 |

(Continued)

OTHER PUBLICATIONS

Dang, Stephen M; et al; "Efficiency of Embryoid Body Formation and Hematopoietic Development from Embryonic Stem Cells in Different Culture Systems" Biotechnology and Bioengineering, 78, 442-453, 2002 (Year: 2002).*

(Continued)

*Primary Examiner* — David W Berke-Schlessel
(74) *Attorney, Agent, or Firm* — Oliff PLC

(57) ABSTRACT

A culture method (a preservation method) of somatic stem cells does not use a chemical such as DMSO that affects a differentiation function of somatic stem cells. A material for an undifferentiated state-maintaining culture for a somatic stem cell, having a naturally occurring polysaccharide; a culture liquid in which the material for the undifferentiated state-maintaining culture is dispersed; a somatic stem cell-containing culture liquid in which the somatic stem cell is (Continued)

suspended in the culture liquid; and a culture method for mesenchymal stem cells in which a naturally occurring polysaccharide is used.

7 Claims, 10 Drawing Sheets

(56) References Cited

FOREIGN PATENT DOCUMENTS

| JP | 4385076 B2 | 12/2009 |
|---|---|---|
| JP | 2010-532167 A | 10/2010 |
| JP | 2012-517823 A | 8/2012 |
| JP | 2013-541956 A | 11/2013 |
| JP | 2013-247943 A | 12/2013 |
| WO | 2008/026634 A1 | 3/2008 |
| WO | 2011/040500 A1 | 4/2011 |
| WO | 2012/131733 A2 | 10/2012 |
| WO | 2013/077423 A1 | 5/2013 |
| WO | 2014017513 A1 | 1/2014 |

OTHER PUBLICATIONS

Gelain, Fabrizio; et al; "Designer Self-Assembling Peptide Nanofiber Scaffolds for Adult Mouse Neural Stem Cell 3-Dimensional Cultures" PLoS One, 1, e119, 2006 (Year: 2006).*

Engler, Adam J. et al. "Matrix Elasticity Directs Stem Cell Lineage Specification". Cell, vol. 126., pp. 677-689, 2006.

Winer, Jessamine P. et al. "Bone Marrow-Derived Human Mesenchymal Stem Cells Become Quiescent on Soft Substrates but Remain Responsive to Chemical or Mechanical Stimuli". Tissu Engineering: Part A, vol. 15, No. 1, pp. 147-154, 2009.

Tremp, Mathias et al. "Adipose-Derived Stem Cells (ASCs) for Tissue Engineering". Regenerative Medicine and Tissue Engineering-Cells and Biomaterials Intech, pp. 179-194, 2011.

Young, David A, et al. "Expression of metalloproteinases and inhibitors in the differentiation of P19CL6 cells into cardiac myocytes". Biochemical and Biophysical Research Communications, vol. 322., pp. 759-765, 2004.

Lou, Yan-Ru et. al. "The use of Nanofibrillar Cellulose Hydrogel as a Flexible Three-Dimensional Model to Culture Human Pluripotent Stem Cells". Stem Cells and Development, vol. 23, No. 4, pp. 380-392, 2014.

Otsuji, Tomomi G. "A 3D Sphere Culture System Containing Functional Polymers for Large-Scale Human Pluripotent Stem Cell Production". Stem Cell Reports, vol. 2., pp. 734-745, 2014.

Apr. 28, 2015 Written Opinion issued in International Patent Application No. PCT/JP2015/051929.

Apr. 15, 2015 Search Report issued in International Patent Application No. PCT/JP2015/051929.

Jun. 22, 2017 extended Search Report issued in European Patent Application No. 15740165.4.

Cao, Haoqing et al. "The application of nanofibrous scaffolds in neural tissue engineering". Advanced Drug Delivery Reviews, vol. 61., pp. 1055-1064, 2009.

Thirumala, Sreedhar et al. "Methylcellulose Based Thermally Reversible Hydrogel System for Tissue Engineering Applications". Cells. vol. 2, No. 3, pp. 460-475, 2013.

Jul. 11, 2018 Office Action issued in European Application No. 15740165.4.

* cited by examiner

FIG. 1
| | ※1 CONCEN-TRATION | CULTURE PERIOD | PHASE-CONTRAST MICROSCOPIC OBSERVATION | Calcein-AM[a] | PI[b] |
|---|---|---|---|---|---|
| EXAMPLE 1 MC1 | 0.05% | 1 WEEK | 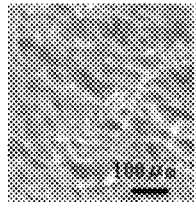 | 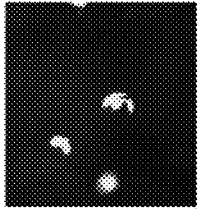 | 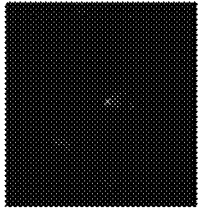 |
| | | 2 WEEKS | 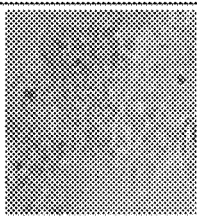 | 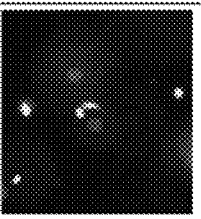 | 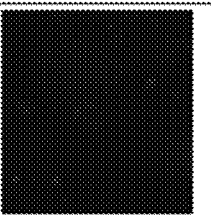 |
| | | 4 WEEKS | 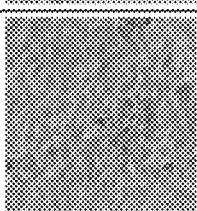 | 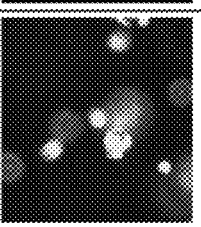 | 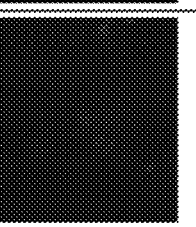 |
| EXAMPLE 2 MC2 | 0.05% | 1 WEEK | 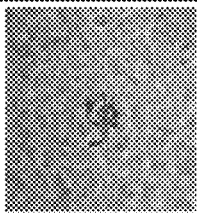 | 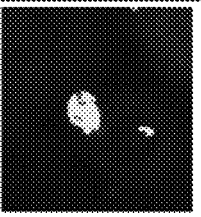 | 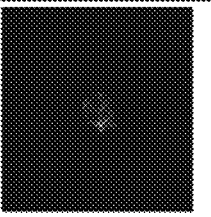 |
| | | 2 WEEKS | 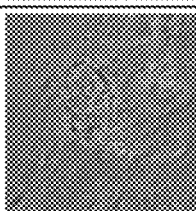 | 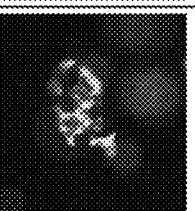 | 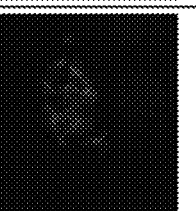 |
| | | 2 WEEKS | 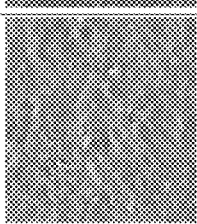 | 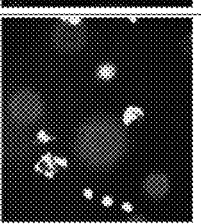 | 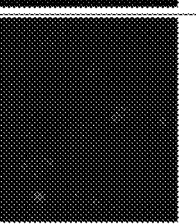 |
※ ALL THE SCALES OF THE IMAGES IN THE TABLE AR IDENTICAL
※1 THE CONCENTRATION OF CELLULOSE NANOFIBERS IN THE CULTURE LIQUID (%W/V))
a): (GREEN FLUORESCENCE/LIVING CELLS)
b): (RED FLUORESCENCE/DEAD CELLS)

FIG. 2

| | ※1 CONCEN- TRATION | CULTURE PERIOD | PHASE-CONTRAST MICROSCOPIC OBSERVATION | Calcein-AM[a] | PI[b] |
|---|---|---|---|---|---|
| EXAMPLE 3 MC3 | 0.05% | 3 WEEKS | | | |
| | | 4 WEEKS | | | |
| EXAMPLE 4 PC | 0.10% | 1 WEEK | | | |
| EXAMPLE 5 BC | 0.10% | 1 WEEK | | | |
| EXAMPLE 6 ME | 0.50% | 1 WEEK | | | |
| EXAMPLE 7 DU | 0.20% | 2 WEEKS | | | |

※. ALL THE SCALES OF THE IMAGES IN THE TABLE ARE IDENTICAL TO THE SCALES IN FIG. 1.

※1 THE CONCENTRATION OF CELLULOSE NANOFIBERS OR POLYSACCHARIDE THICKENERS IN THE CULTURE LIQUID (%W/V)

a): (GREEN FLUORESCENCE/LIVING CELLS)

b): (RED FLUORESCENCE/DEAD CELLS)

FIG. 3

| | | (CONTROL TEST) 6 TIME-PASSAGED hMSC | EXAMPLE 1 MC1 (NF CONCENTRATION: 0.025%) | EXAMPLE 2 MC2 (NF CONCENTRATION: 0.025%) | EXAMPLE 3 MC3 (NF CONCENTRATION: 0.05%) |
|---|---|---|---|---|---|
| POSITIVE MARKER | STRO-1 | | | | |
| | CD29 | | | | |
| | CD44 | | | | |
| | CD73 | | | | |
| | CD90 | | | | |
| | CD105 | | | | |

※ IN THE FIGURE, NF CONCENTRATION REFERS TO THE CONCENTRATION OF CELLULOSE NANOFIBERS IN THE CULTURE LIQUID( % (w/v) ).
ALL THE SCALES OF THE IMAGES IN THE TABLE ARE IDENTICAL.

FIG. 4

| PRIMARY ANTIBODY | | (CONTROL TEST) 6 TIME-PASSAGED hMSC | EXAMPLE 1 MC1 (NF CONCENTRATION: 0.025%) | EXAMPLE 2 MC2 (NF CONCENTRATION: 0.025%) | EXAMPLE 3 MC3 (NF CONCENTRATION: 0.05%) |
|---|---|---|---|---|---|
| NEGATIVE MARKER | CD11b | | | | |
| | CD14 | | | | |
| | CD19 | | | | |
| | CD34 | | | | |
| | CD45 | | | | |

※ IN THE FIGURE, NF CONCENTRATION REFERS TO THE CONCENTRATION OF CELLULOSE NANOFIBERS IN THE CULTURE LIQUID( % (w/v) ).
ALL THE SCALES OF THE IMAGES IN THE TABLE ARE IDENTICAL TO THE SCALES IN FIG. 3.

FIG. 5

| NC[a] CONCENT-RATION | CULTURE PERIOD | PHASE-CONTRAST MICROSCOPIC OBSERVATION | Calcein-AM[a) | PI[b) |
|---|---|---|---|---|
| CONTROL TEST DMEM | 1 WEEK | | | |

※ IN THE FIGURE, NC CONCENTRATION REFERS TO THE CONCENTRATION OF CELLULOSE NANOFIBERS IN THE CULTURE LIQUID (% BY MASS))

a): (GREEN FLUORESCENCE/LIVING CELLS)
b): (RED FLUORESCENCE/DEAD CELLS)

FIG. 6
| | | (CONTROL TEST) 6 TIME-PASSAGED hMSC | EXAMPLE 11 MC5 (NF CONCENTRATION: 0.02%) |
|---|---|---|---|
| POSITIVE MARKER | STRO-1 | 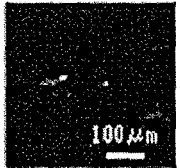 100 μm | 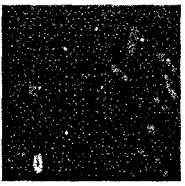 |
| | CD29 | 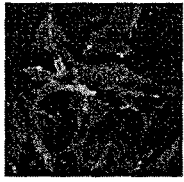 | 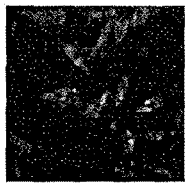 |
| | CD44 |  |  |
| | CD73 |  |  |
| | CD90 |  |  |
| | CD105 | 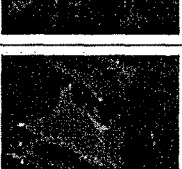 | 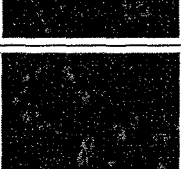 |
※ IN THE FIGURE, NF CONCENTRATION REFERS TO THE CONCENTRATION OF CELLULOSE NANOFIBERS IN THE CULTURE LIQUID (% BY MASS).
ALL THE SCALES OF THE IMAGES IN THE TABLE ARE IDENTICAL.

FIG. 7
| PRIMARY ANTIBODY | | (CONTROL TEST) 6 TIME-PASSAGED hMSC | EXAMPLE 12 MC5 (NF CONCENTRATION: 0.02%) |
|---|---|---|---|
| NEGATIVE MARKER | CD11b |  |  |
| | CD14 | 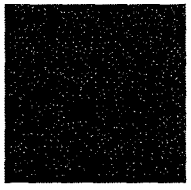 | 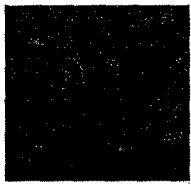 |
| | CD19 |  |  |
| | CD34 | 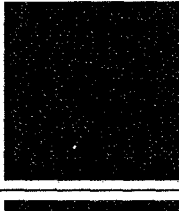 |  |
| | CD45 | 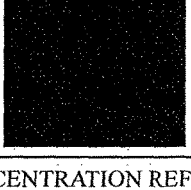 |  |
※ IN THE FIGURE, NF CONCENTRATION REFERS TO THE CONCENTRATION OF CELLULOSE NANOFIBERS IN THE CULTURE LIQUID (% BY MASS).
ALL THE SCALES OF THE IMAGES IN THE TABLE ARE IDENTICAL TO THE SCALES IN FIG. 6.

※1 WITH A DIFFERENTIATION INDUCING AGENT
※2 WITHOUT A DIFFERENTIATION INDUCING AGENT
※3 WITHOUT A PRIMARY ANTIBODY
※4 WITH A PRIMARY ANTIBODY

※1 WITH A DIFFERENTIATION INDUCING AGENT
※2 WITHOUT A DIFFERENTIATION INDUCING AGENT

※1  WITH A DIFFERENTIATION INDUCING AGENT
※2  WITHOUT A DIFFERENTIATION INDUCING AGENT

※1 WITH A DIFFERENTIATION INDUCING AGENT
※2 WITHOUT A PRIMARY ANTIBODY

※1 WITH A DIFFERENTIATION INDUCING AGENT
※2 WITHOUT A PRIMARY ANTIBODY

MATERIAL FOR UNDIFFERENTIATED STATE-MAINTAINING CULTURE

TECHNICAL FIELD

The present invention relates to a material for culturing somatic stem cells while maintaining an undifferentiated state of the cells, particularly to a culture material containing, a naturally occurring polysaccharide, which can suppress ex vivo differentiation of somatic stem cells such as mesenchymal stem cells to keep those cells in a state where proliferation and differentiation thereof are arrested (a resting condition) during a certain time period, for example, during a time period required for a treatment.

BACKGROUND ART

Mesenchymal stem cells (MSCs) are one of somatic stem cells (also referred to as biogenic stem cells or tissue stem cells) that may be differentiated into mesenchymal cells, such as osteoblasts, adipocytes, myocytes, chondrocytes, neurons, and hepatocytes. MSCs are expected to be applied for treatments in regenerative medicine in which tissues are remodeled or repaired. Examples of such treatments include anti-inflammation and immunosuppression, tissue repair, improvement of blood flow by angiogenesis, and anti-senescence (anti-aging). MSCs are also expected to be applied for treatments of disorders that have had no cures conventionally.

Multipotent mesenchymal stem cells can be separated not only from patient's tissues, such as bone marrows, adipose tissues, synovial membranes, alveolar bones, and periodontal ligaments, but also from various cells, such as placentas, umbilical cord blood, and umbilical cords, and thus the height of a bioethical hurdle to be cleared in order to use mesenchymal stem cells is low. Also because oncogenicity of mesenchymal stem cells may be lower than that of ES cells or iPS cells, an early clinical application of mesenchymal stem cells are expected.

When mesenchymal stem cells are clinically applied as cell and tissue pharmaceuticals or cell and tissue medical devices, for example, when these are applied to autologous transplantation, the application includes the steps of separating cells from a patient body, culturing the cells ex vivo to proliferate them, and autografting the cells to the patient. In this case, it is important to secure effectiveness and safety of the cells returned to the patient without any transformations to cells having characteristics which are other than the object during the time of culturing and/or preserving. However, quality of mesenchymal stem cells is hard to be controlled because they tend to be easily differentiated or aged, and thus quality control of these cells is a large issue.

In order to facilitate proliferation of mesenchymal stem cells cultured ex vivo, various proliferation peptides have been investigated (Patent Documents 1 and 2). Also, it is reported that when specific growth factors and a fatty acid complex are added to a serum-free basic medium, cell proliferation is comparable to, or even beyond the case where a serum-added medium is used (Patent Document 3). Meanwhile, it has been known that mesenchymal stem cells are divided in a limited number, and cells proceed to be aged depending on the number of divisions. Even now, how many divisions to induce proliferation are allowed to assure effectiveness of, that is, quality in clinical applications of mesenchymal stem cells is still not confirmed.

Therefore, mesenchymal stem cells collected from a patient are strongly desired to be preserved with high quality without deterioration until they are used for treatments. Without limiting to mesenchymal stem cells, a preservation method in which cells are cryopreserved at a temperature of liquid nitrogen is commonly used. Freezing and thawing will lose activities and functions of cells, and thus a chemical such as dimethyl sulfoxide (DMSO) is added to a freezing medium in order to protect cells during processes of freezing and thawing. DMSO is highly membrane-permeable and lowers ice crystal formation in the process in which cells are frozen to minimize damage of membranes and dehydration of organelles (Patent Document 4).

As an approach to preserve mesenchymal stem cells other than the freezing method, the cells may be preserved as cultured normally without freezing. However, the problem is that natures and characteristics of mesenchymal stem cells may be changed under a culture environment.

Generally, extracellular matrices constituting a surrounding environment of cells in vivo are known to chemically and physically affect differentiation states of connective tissue cells, and are reported to also affect determination of lineages that mesenchymal stem cells are differentiated into.

For example, induction of mesenchymal stem cells to be differentiated into neurologic, myogenic, or osteogenic cells by culturing the mesenchymal stem cells on a hydrogel having elasticity controlled to be similar to that of an in vivo biological environment has been investigated (Non-Patent Document 1). This finding means that mesenchymal stem cells will differentiate into lineages depending on characteristics of elasticity and the like in a culture environment, only by culturing the cells on a hydrogel substrate having, an elastic, modulus of 1 kPa or above, which means that the undifferentiated state of the mesenchymal stem cells is collapsed, and a quality of the cells will be deteriorated.

Meanwhile, a method in which mesenchymal stem cells are cultured on a type I collagen and fibronectin-coated acrylamide gel having elasticity of 250 Pa in order to introduce or keep the cell cycle of the stem cells in a static state to maintain biological activities of the cells, has been proposed (Non-Patent Document 2 and Patent Document 5).

PRIOR ART DOCUMENTS

Patent Documents

Patent Document 1: International Publication WO 2008/026634 Pamphlet
Patent Document 2: International Publication WO 2011/040500 Pamphlet
Patent Document 3: Japanese Patent No. 4385074 (JP 4385076 B2)
Patent Document 4: Japanese Translation of PCT International Application publication No. 2012-.517823 (JP 2012-517823 A)
Patent Document 5: Japanese Translation of PCT International Application publication No. 2010-532167 (JP 2010-532167 A)

Non-Patent Documents

Non-Patent Document 1: Cell 126, 677, 2006
Non-Patent Document 2: Tissu Eng Part A 15, 147, 2009
Non-Patent Document 3: REGENERATIVE MEDICINE AND TISSUE ENGINEERING-CELLS AND BIOMATERIALS, Daniel Eberli, 2011 InTech
Non-Patent Document 4. Biochem. Biophys. Res. Commun., 322 (3), 759-765 (2004)

SUMMARY OF THE INVENTION

Problem to be Solved by the Invention

For the aforementioned cryopreservation method in which a chemical such as DMSO is used in a freezing medium, it has been reported that cells are seriously damaged in as thawing process (Non-Patent Document 3), and that differentiation of mesenchymal stem cells may be affected (Non-Patent Document 4).

Also, for the aforementioned differentiation induction in which a hydrogel is used as an extracellular matrix, cells in a static state and a preservation ability of the cells have not been found because the elasticity of the culture substrate under consideration is in a higher range.

In addition, it has been pointed out that acrylamide monomers constituting an acrylamide gel that has been proposed as a culture substrate are neurotoxic and hepatotoxic. Generally, biocompatible water-soluble polymers and polymerizable monomers constituting a hydrogel usually show cell toxicities, and completely removing unreacted monomers from a polymeric gel obtained from such monomers is actually difficult. Therefore, such a polymeric gel is problematic to be used as a cell culture substrate that requires biosafety.

As mentioned, there have been various proposals to improve viability of mesenchymal stem cells during preservation while keeping multipotency thereof. However, for mesenchymal stem cells, any preservation methods that satisfy a preservation ability of desired cells, that are not cytotoxic, and that can be used instead of the cryopreservation method in which a chemical such as DMSO is used, have not been proposed.

The present invention has been made in view of the circumstances of such prior arts, and a problem to be solved by the present invention is to provide a culture method (a preservation method) of somatic stem cells without using a chemical such as DMSO that affects a differentiation function of somatic stem cells. The culture method hardly deteriorates a differentiation function and a cellular function, and hardly affects viability, and thus can be used instead of the conventional cryopreservation method.

Means for Solving the Problem

As a result of intensive study to solve the problems described above, the present inventors have found that, by dissolving or dispersing a naturally occurring polysaccharide functioning as a thickener or a gelling agent, for example, a polysaccharide thickener or a nanofibrous polysaccharide in a culture liquid in which somatic stem cells are cultured, the polysaccharide can be a scaffold that allows stem cells to be cultured in a resting condition, which means that lineage determination involving differentiation of the stem cells is almost inactive. That is, the present inventors have found that, by dissolving or dispersing mesenchymal stem cells in a cell culture liquid, in which a naturally occurring polysaccharide is dissolved or dispersed such that the cells are suspended in the culture liquid, differentiation of mesenchymal stem cells is suppressed under the culture condition, and that the cells can be preserved while maintaining their initial state for a certain time period (culturing in a resting condition) without freezing the culture liquid. The initial state herein refers to an undifferentiated state where mesenchymal stem cells have not started to differentiate into any differentiation lineages yet. Moreover, the present inventors have found that, by using a naturally occurring polysaccharide, such as the polysaccharide thickener or nanofibrous polysaccharide, mesenchymal stem cells can be harvested from the culture liquid according to a general method for harvesting cells using protease or the like, and the harvested mesenchymal stem cells can be used again, and whereby the present invention has been completed.

That is, the present invention belongs to a cell culture method using a naturally occurring polysaccharide, and the present invention is particularly based on a unique finding in which this culture system enables an undifferentiated state-maintaining culture for mesenchymal stem cells. The present invention has been completed by finding the structure of the polysaccharide and optimal conditions of solutions or dispersion liquids thereof that enable such a culture.

The principle of the undifferentiated state-maintaining culture for mesenchymal stem cells in the present invention is as follows. Culturing mesenchymal stem cells in a resting condition by fixing their cell cycles in a quiescent phase allows not only shortening of cell lives and progression of senescence caused by cell division and proliferation to be prevented, but also possibilities of cell transformations caused by differentiation into undesirable phenotypes to be excluded. Such a culture condition is close to a living condition where mesenchymal stem cells are placed in as natural extracellular environment in vivo, which is referred to as a stem cell niche, and thus the culture method according to the present invention solves the problem by procedures mimicking an in vivo situation.

In addition, the present invention includes avoidance of deteriorated quality of mesenchymal stem cells caused by the resting culture, establishment of a harvest method used after cancelling the resting condition, and confirmation of quality maintenance of the harvested mesenchymal stem cells. Quality maintenance and harvest are necessary in order to keep and use high-quality mesenchymal stem cells, and the present invention solves these problems by using a naturally occurring polysaccharide.

Specifically, as a first aspect, the present invention relates to a material for an undifferentiated state-maintaining cattle for a somatic stem cell, which comprises a naturally occurring, polysaccharide.

As a second aspect, the present invention relates to the material for the undifferentiated state-maintaining culture according to the first aspect, in which the polysaccharide is a nanofibrous polysaccharide.

As a third aspect, the present invention relates to the material for the undifferentiated state-maintaining culture according to the first aspect, in which the polysaccharide is a polysaccharide thickener.

As a fourth aspect, the present invention relates to the material for the undifferentiated state-maintaining culture according to the third aspect, in which the polysaccharide thickener is methylcellulose or diutan gum.

As a fifth aspect, the present invention relates to the material for the undifferentiated state-maintaining culture according to any one of the first to the fourth aspects, in which the somatic stem cell is a mesenchymal stem cell.

As a sixth aspect, the present invention relates to the material for the undifferentiated state-maintaining culture according to any one of the first to the fifth aspects, in which an undifferentiated state and multipotency of the somatic stem cell cultured for 1 day to 30 days under a culture condition of 37° C. and 5% by volume carbon dioxide atmosphere are maintained at comparable degrees to an undifferentiated state and multipotency of the somatic stem cell immediately after collection.

As a seventh aspect, the present invention relates to the material for the undifferentiated state-maintaining culture according to any one of the first to the sixth aspects, in which the somatic stem cell cultured under the culture condition can be harvested by treating with an enzyme.

As an eighth aspect, the present invention relates to the material for the undifferentiated state-maintaining culture according to any one of the second aspect and the fifth to the seventh aspects, in which the polysaccharide is in the form of nanofiber having an average fiber diameter (D) of 1 nm to 100 nm.

As a ninth aspect, the present invention relates to the material for the undifferentiated state-maintaining culture according to any one of the second aspect and the fifth to the eighth aspects, in which the polysaccharide is in the form of nanofiber having an average particle size (d) of 0.01 μm to 10 μm.

As a tenth aspect, the present invention relates to the material for the undifferentiated state-maintaining culture according to the eighth aspect, in which the polysaccharide is in the firm of nanofiber in which a ratio of an average fiber length (L) to an average finer diameter (D) (L/D) is 2 to 500.

As an eleventh aspect, the present invention relates to the material for the undifferentiated state-maintaining culture according to any one of the second aspect and the fifth to the tenth aspects, in which the undifferentiated state-maintaining culture is a natural nanofiber derived from cellulose.

As a twelfth aspect, the present invention relates to a culture liquid, in which the material for the undifferentiated state-maintaining culture as described in any one of the first to the eleventh aspects is dissolved or dispersed in a liquid.

As a thirteenth aspect, the present invention relates to the culture liquid according to the twelfth aspect, in which the material for the undifferentiated state-maintaining culture is dissolved or dispersed at a concentration of 0.0001% (w/v) to 2% (w/v) to a total volume of the culture liquid.

As a fourteenth aspect, the present invention relates to a somatic stem cell-containing culture liquid, in which the somatic stem cell is suspended in the culture liquid as described in the twelfth aspect or the thirteenth aspect.

As a fifteenth aspect, the present invention relates to the somatic stem cell-containing culture liquid according to the fourteenth aspect, in which the material for the undifferentiated state-maintaining culture is suspended in the culture liquid at a concentration of 0.0001% (w/v) to 2% (w/v) to a total volume of the somatic stem cell-containing culture liquid containing $1.0 \times 10^3$ to $1.0 \times 10^6$ of stem cells in a unit volume (1 mL).

As a sixteenth aspect, the present invention relates to the somatic stem cell-containing culture liquid according to the fourteenth aspect or the fifteenth aspect, further comprising a serum.

As a seventeenth aspect, the present invention relates to the somatic stem cell-containing culture liquid according to the sixteenth aspect, in which the serum is selected from the group consisting of fetal bovine sera, human sera, horse sera, and chicken sera.

As an eighteenth aspect, the present invention relates to the somatic stem cell-containing culture liquid according to the sixteenth aspect or the seventeenth aspect, in which the serum is contained at a concentration of 0.1% by volume to 50% by volume to a total volume of the somatic stem cell-containing culture liquid.

As a nineteenth aspect, the present invention relates to the somatic stem cell-containing culture liquid according to any one of the fourteenth to the eighteenth aspects, further comprising as cellular function regulatory factor.

As a twentieth aspect, the present invention relates to a culture method for mesenchymal stem cells characterized in that an undifferentiated state and multipotency of a mesenchymal stem cell cultured for 1 day to 30 days are maintained at comparable degrees to an undifferentiated state and multipotency of the mesenchymal stem cell immediately after collection by culturing the mesenchymal stem cell ex vivo in a presence of a naturally occurring polysaccharide.

Effects of the Invention

According to the material for the undifferentiated state-maintaining culture of the present invention, mesenchymal stem cells that are especially useful in regenerative medicine can be preserved for a long time period while maintaining an undifferentiated state (resting condition) of the cells without addition of chemicals, proteins, control factors, and the like to the medium as well as removal of growth factors.

Also, by using the material for the undifferentiated state-maintaining culture of the present invention, mesenchymal stem cells collected from a living body, which are then selected and purified, can be maintained in high-quality until using them for an actual treatment. "Maintained in high-quality" herein means that an undifferentiated state and multipotency that are characteristics defining stem cells are maintained. In addition, according to the culture method for mesenchymal stem cells of the present invention, higher cell recovery rate of mesenchymal stem cells can be achieved after a preservation culture of the cells for a certain time period. In order to harvest the cells, any special procedures are not required, and a method commonly used in the art of cell culture, for example, a method using a protease such as trypsin can be used.

Thus, the material for the undifferentiated state-maintaining culture of the present invention has two main effects, that is, a preservation culture that maintains mesenchymal stem cells in high-quality, and ease of harvest and preparation of the cells at the time of use.

BRIEF DESCRIPTION OF THE DRAWINGS

FIG. 1 is a figure showing results of viability determinations in hMSC cultures of Examples 1 and 2 conducted by a calcein-AM/PI method.

FIG. 2 is a figure showing results of viability determinations in hMSC cultures of Examples 3 to 7 conducted by a calcein-AM/PI method.

FIG. 3 is a figure showing results of positive marker staining of hMSCs cultured for 4 weeks in Examples 1 to 3.

FIG. 4 is a figure showing results of negative marker staining of hMSCs cultured for 4 weeks in Examples 1 to 3.

FIG. 5 is a figure showing the result of a viability determination in an hMSC culture (1 week) of a control test conducted by a calcein-AM/PI method.

FIG. 6 is a figure showing results of positive marker staining of hMSCs cultured for 4 weeks in Example 12.

FIG. 7 is a figure showing results of negative marker staining of hMSCs cultured for 4 weeks in Example 12.

MODES FOR CARRYING OUT THE INVENTION

Figure 8:
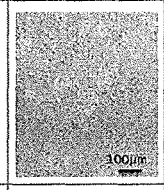
FIG. 8 is a figure showing results of immunostaining tests of hMSCs by using an anti-FABP4 antibody. The hMSCs were cultured in Example 8, and were then subjected to an adipocyte differentiation inducing test.

Hereinafter, the material for the undifferentiated state-maintaining culture of the present invention will be explained in detail.

Note that, in the "resting culture," stem cells under the ex vivo culture condition are maintained in a state in which cell cycles of these stem cells are in a quiescent phase, and the cells have not been differentiated, which are characteristics of stem cells when they are in vivo. That is, the "resting culture" herein refers to a culture maintaining stem cells in an undifferentiated state (initial state) (placing the cells in a resting condition).

<Material for Undifferentiated State-Maintaining Culture>

The material for the undifferentiated state-maintaining culture of the present invention contains a naturally occurring polysaccharide, and the polysaccharide is preferably a nanofibrous polysaccharide (hereinafter, it will be simply referred to as "nanofiber") or a polysaccharide thickener.

[Source of Nanofiber (Cellulose)]

An example of the naturally occurring nanofiber used in the material for the undifferentiated state-maintaining culture of the present invention is a refined cellulose nanofiber.

Examples of a source of the cellulose nanofiber to be used include cellulose derived from plants including wood, bamboo, hemp, jute, kenaf, cotton, crops, and food residues; and cellulose produced by microorganisms or animals, such as bacterial cellulose, *Cladophora* cellulose, *Glaucocystis* cellulose, *Valonia* cellulose, and ascidian cellulose.

The cellulose derived from plants is formed as follows: extremely thin fibers that are referred to as microfibrils form bundles, and then higher order structures are formed in a stepwise manner from fibrillar to lamellar, and fibrous cells. In the bacterial cellulose, microfibrils of cellulose secreted from microbial cells form a fine mesh structure while maintaining sizes of the microfibrils.

Preferable examples of a source of the cellulose nanofiber used as the material for the undifferentiated state-maintaining culture of the present invention include cellulose prepared by processing the cellulose derived from plants including crops and food residues or cellulose produced by microorganisms or animals by conducting a kraft pulp method or a sulfite pulp method; and powder cellulose prepared by pulverizing these celluloses by using a high-pressure homogenizer, a mill, or the like. A more preferable example is crystalline cellulose obtained by removing non-crystal portions with an acid hydrolysis treatment, and then performing pulverization and sieving.

[Method for Refining (Pulverizing) Source of Cellulose]

As mentioned above, refined cellulose nanofibers obtained by pulverizing these sources of cellulose are preferably used in the present invention. Although a method for pulverizing sources of cellulose is not limited, a method giving strong shear force, for example, a high-pressure homogenizer, a grinder (millstone), or a medium stirring mill such as a bead mill is preferable in order to allow the later-mentioned fiber diameters and fiber lengths of refinement, which meet the purpose of the present invention.

Among these pulverization methods, a refinement (pulverization) is preferably performed by a method using a high-pressure homogenizer, such as a wet mill method described in Japanese Patent Application Publication No. 2005-270891 (JP 2005-270891 A) or Japanese Patent Publication No. 5232976 (JP 5232976 B2). Specifically, a dispersion liquid (aqueous dispersion liquid) in which a source or cellulose is dispersed is sprayed at a high-pressure from each of a pair of nozzles to hit them each other, so that the source of cellulose is pulverized. Such a pulverization can be performed by using, for example, Star Burst (registered trademark) system (a high-pressure pulverization device manufactured by Sugino Machine Limited) and Nanovater (registered trademark) (a high-pressure pulverization device manufactured by YOSHIDA KIKAI Co., Ltd.).

When a source of cellulose is refined (pulverized) by using the aforementioned high-pressure homogenizer, degrees of refinement and homogenization depend on the pressure to force feed the source to an ultrahigh-pressure chamber of the high-pressure homogenizer, the number of times of passing through the ultrahigh-pressure chamber (the number of times of the processes), and a cellulose concentration in the aqueous dispersion liquid.

The force feed pressure (processing pressure) is usually 50 MPa to 250 MPa, and is preferably 150 MPa to 245 MPa. If the force feed pressure is below 50 MPa, cellulose is not satisfactory refined, and thus expected effects cannot be obtained.

Meanwhile, at the time of a refinement process, a cellulose concentration in an aqueous dispersion liquid is 0.1% by mass to 30% by mass, and is preferably 1% by mass to 10% by mass. If a cellulose concentration in the aqueous dispersion liquid is below 0.1% by mass, productivity will be extremely low, and if the cellulose concentration is over 30% by mass, pulverization efficiency will be low, and thus desired cellulose nanofibers cannot be obtained.

The number of times of the refinement (pulverization) processes is not particularly limited, and depends on a cellulose concentration in the aqueous dispersion liquid. For example, when the cellulose concentration is 0.1% by mass to 1% by mass, the number of times of the refinement is about 1 to 100; and when the cellulose concentration is 1% by mass to 10% by mass, the number of times of the refinement is 1 to 1,000, preferably 10 to 200. From an industrial view, a dispersion liquid having a high cellulose concentration such as over 30% by mass is not realistic, because the dispersion liquid requires several thousand times of the refinement process, and becomes highly viscous and hard to be handled.

An average particle size (d) of a cellulose nanofiber used in the present invention is 0.01 μm to 10 μm, and is preferably 0.05 μm to 5 μm. In the present invention, "an average particle size" of a cellulose nanofiber refers to a fluid dynamical diameter of the cellulose nanofiber dispersed in water under the dilute condition, which is in the random coil state. If the average particle size is below 0.01 μm, the addition effects are not obtained because the cellulose nanofiber is too fine, and thus a cell-suspending effect of the material for the undifferentiated state-maintaining culture, which contains the cellulose nanofibers, is lowered, and cell recovery rate is also lowered. If the average fiber diameter is larger than 10 μm, transparency and a cell-dispersion effect of the material for the undifferentiated state-maintaining culture are lost. In this case, cells are aggregated each other and/or the material for the undifferentiated state-maintaining culture is precipitated with the cells, and thus expected effects cannot be obtained.

An average fiber diameter (D) of a cellulose nanofiber used in the present invention is 1 nm to 100 nm, preferably 5 nm to 70 nm, and more preferably 10 nm to 50 nm. If the average fiber diameter is below 1 nm, the addition effects are not obtained because the cellulose nanofiber is too fine, and thus the rate of cell recovery from the material for the undifferentiated state-maintaining culture, which contains the cellulose nanofibers, is lowered. If the average fiber diameter is larger than 100 nm, a cell-dispersion effect of the material for the undifferentiated state-maintaining culture is lost. In this case, cells are aggregated each other, and thus expected effects cannot be obtained.

An average fiber length (L) of a cellulose nanofiber used in the present invention is 0.01 μm to 100 μm, and is preferably 0.05 μm to 10 μm.

An aspect ratio (L/D) of a cellulose nanofiber used in the present invention can be determined by an average fiber length/an average fiber diameter, and is usually 2 to 500, preferably 3 to 300, and more preferably 4 to 250. If the aspect ratio is less than 2, dispersibility of the material for the undifferentiated state-maintaining culture is not satisfactory stable, and dispersibility of cells cannot be maintained. If the aspect ratio is more than 500, the fiber length becomes extremely large, and the culture liquid becomes viscous, which induces significant deterioration of the handling property.

In the present invention, an average particle size (d), an average fiber diameter (D), and an average fiber length (L) of the cellulose nanofiber are determined as follows.

An average particle size (d): a cellulose dispersion liquid prepared in the later-mentioned Production Examples was diluted to 0.01% by mass to 0.1% by mass with ultrapure water, and was dispersed in a ultrasound bath for 30 minutes. An average particle size (d) was then measured by using the dynamic light scattering spectrometer (FDLS-3000, the cumulant method) manufactured by Otsuka Electronics Co., Ltd. or the laser diffraction particle size analyzer (Mastersizer 2000, a passage diameter of 50% cumulative volume (D50)) manufactured by Malvern Instruments Ltd.

Note that the average particle size (d) can be obtained as a fluid dynamical diameter from the diffusion coefficient (D) according to the Stokes-Einstein equation below $$d = kT/3\, \pi \eta_0 D$$

d: a particle size (a fluid dynamical diameter), k: Boltzmann constant, T: an absolute temperature, $\eta_0$: viscosity of the solvent.

An average fiber diameter (D): a collodion supporting membrane manufactured by Okenshoji Co., Ltd. was hydrophilized for 3 minutes in an ion cleaner (JIC-410) manufactured by JEOL Ltd. A few drops of a cellulose dispersion liquid prepared in the later-mentioned Production Examples (diluted with ultrapure water) were dropped onto the supporting membrane, and were dried at a room temperature to prepare a sample. The sample was observed on as transmission electron microscopy (TEM, H-8000) manufactured by Hitachi, Ltd. (10,000 magnifications) at the accelerating voltage of 200 kV. A fiber diameter was measured for each of 200 samples to 250 samples of the cellulose nanofibers by using the obtained images, and a number average value thereof was obtained as an average fiber diameter (D).

An average fiber length (L): a cellulose dispersion liquid prepared in the later-mentioned Production Examples was diluted with dimethyl sulfoxide (DMSO) so that the cellulose concentration became 0.001% by mass to disperse cellulose. The cellulose dispersion liquid was cast onto a silicon wafer whose surface was previously hydrophilized with concentrated sulfuric acid, and was dried at 110° C. for 1 hour to prepare a sample. The obtained sample was observed on a scanning electron microscopy (SEM, JSM-7400F) manufactured by JEOL Ltd. (2,000 magnifications) to obtain images, and a fiber length was measured for each of 150 samples to 250 samples of the cellulose nanofibers b using the obtained images, and a number average value thereof was obtained as an average fiber length (L).

[Polysaccharide Thickener]

Polysaccharide thickeners such as naturally occurring methylcellulose and diutan gum act as thickeners at high concentrations. Meanwhile, at low concentrations such as 1% or below, the polysaccharide thickeners act as dispersants for cells or the like. It is known that when these polysaccharide thickeners are used in cell cultures at low concentrations, cell proliferation are allowed to be stable without largely affecting handlings such as culture procedures. In this case, the polysaccharide thickener added at low viscosity (as a sort of dispersant) acts to suppress adhesion of cells to culture vessels, formation of cell clusters in which cells adhere to each other, and the like. By this action, loss of cell function and inhibition of proliferation caused by cell adhesion, as well as necrosis caused by nutrient deficiency and oxygen deficiency in the core of the cell cluster can be suppressed.

Preferable examples of the naturally occurring polysaccharide thickeners used in the material for the undifferentiated state-maintaining culture of the present invention include hyaluronic acid, gellan gum, deacylated gellan gum, rhamsan gum, diutan gum, xanthan gum, carrageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate, and salts thereof; alginic acid derivatives, such as sodium alginate and alginic acid propylene glycol ester; methylcellulose, ethylcellulose, hydroxyethylcellulose, hydroxypropylcellulose, carboxymethylcellulose, and salts thereof such as sodium salts; cellulose derivatives, such as methylhydroxypropylcellulose, sodium cellulose sulfate, and dialkyl dimethyl ammonium cellulose sulfate; cationized cellulose such as chitosan and polyquaternium-10, and cationized polysaccharides such as cationized dextran, and guar hydroxypropyltrimonium chloride.

Among them, methylcellulose or diutan gum can preferably be used as the material for the undifferentiated state-maintaining culture of the present invention.

<Somatic Stem Cell>

[Mesenchymal Stem Cell]

Somatic stem cells to which the material for the undifferentiated state-maintaining culture of the present invention is directed for culturing are mesenchymal stem cells (MSCs), hematopoietic stem cells (HSCs), umbilical cord blood stem cells, and nerve stem cells. Among them, the material is particularly directed to mesenchymal stem cells (MSCs).

Mesenchymal stem cells can be differentiated into various types of cells. Usually, mesenchymal stem cells that can be used in treatment are collected from adult bodies, selected, and purified. Mesenchymal stem cells for which the material for the undifferentiated state-maintaining culture of the present invention can be applied are not only primary human mesenchymal stem cells collected directly from a patient for clinical uses, but also mesenchymal stem cells that can be used for research, which are available from cell banks, and immortalized mesenchymal stem cell lines.

As those skilled in the art know, these mesenchymal stem cells may be any cells derived from an autologous source, derived from allogeneic sources, or derived from heterologous sources, from the point of view of clinical applications. Sources for collection can be any of donor bone marrows, tissue biopsies, embryonic sources, and postnatal sources. Specific examples of the sources for collection include bone marrows of iliac crests; femorotibial, spinal, costal, or other's bone marrow cavities; and biopsies of tissues including embryonic yolk sacs, placentas, umbilical cords, periostea, fetal or adolescent skin and blood.

<Culture Liquid>

The present invention also relates to a culture liquid in which the material for the undifferentiated state-maintaining culture is dispersed in a liquid.

The culture liquid includes a buffer and/or a liquid medium.

As the liquid medium, a medium for culturing animal cells among natural media, semisynthetic media, synthetic media, and the like can preferably be used. Examples of the medium include William's E medium. Ham's Nutrient Mixture. F10, Ham's Nutrient Mixture F12, RPMI 1640 medium, Eagle's Minimum Essential Medium (EMEM), Dulbecco's Modified Eagle's Medium (DMEM), and α-Modified Eagle's Medium (α-MEM).

The liquid medium may contain sodium, potassium, calcium, magnesium, phosphorous, chlorine, amino acids, vitamins, cytokines, hormones, antibiotics, serum, fatty acids, and sugars. Also, one or more a other chemical or biological ingredients can be added to the liquid medium in combination, depending on purposes. Examples of the other chemical or biological ingredients that can be added include fetal bovine sera, human sera, horse sera, chicken sera, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors, and cellular function regulatory factors.

The culture liquid, in which the material for the undifferentiated state-maintaining culture is dispersed at a concentration of 0.0001% (w/v) to 2% (w/v), preferably of 0.0005% (w/v) to 1% (w/v) to a total volume of the culture liquid, is preferred.

<Somatic Stem Cell-Containing Culture Liquid>

The present invention further relates to a somatic stem cell-containing culture liquid in which somatic stem cells are suspended in a bath of the culture liquid.

The somatic stem cell-containing culture liquid, in which the material for the undifferentiated state-maintaining culture is suspended in the culture liquid at a concentration of 0.0001% (w/v) to 2% (w/v), preferably of 0.0005% (w/v) to 1% (w/v) to a total volume of the somatic stem cell-containing culture liquid containing $1.0 \times 10^3$ to $1.0 \times 10^6$ of stem cells in a unit volume (1 mL), is preferred.

To the somatic stem cell-containing culture liquid, other chemical or biological ingredients that can be added to the liquid medium, that is, sodium, potassium, calcium, magnesium, phosphorous, chlorine, amino acids, vitamins, cytokines, hormones, antibiotics, serum, fatty acids, sugars, and the like may be added. For example, fetal bovine sera, human sera, horse sera, chicken sera, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, and methylcellulose, as well as various cellular function regulatory factors, the fibroblast growth factor, the epidermal growth factor, the vascular endothelial growth factor, the platelet derived growth factor, the hepatocyte growth factor, and the like can further be added.

For example, a serum, such as a fetal bovine serum, a human serum, a horse serum, and a chicken serum can preferably be added at a concentration of 0.1% by volume to 50% by volume, preferably of 0.5% by volume to 20% by volume to a total volume of the somatic stem cell-containing culture liquid.

[Culture Method]

One example of the culture method (resting culture) for somatic stem cells using the material for the undifferentiated state-maintaining culture of the present invention will be described below.

The material for the undifferentiated state-maintaining culture of the present invention is added to the aforementioned culture liquid (a buffer and/or the liquid medium, or a liquid medium to which a fetal bovine serum, a human serum, or the like is added), and then the material for the undifferentiated state-maintaining culture is dissolved or dispersed in the culture liquid to prepare a solution or a dispersion liquid.

The culture liquid containing, the material for the undifferentiated state-maintaining culture of the present invention thus prepared is placed in a suitable culture vessel commonly used for culturing animal cells, such as a dish, a flask, a well plate, a plastic bag, and a Teflon (registered trademark) bag, and then mesenchymal stem cells suspended in a suitable buffer or the like are seeded thereto, so that the number of the stem cells is $1.0 \times 10^3$ to $1.0 \times 10^6$ in a unit volume (1 mL) of the medium. At this time, a serum, a cellular function regulatory factor, and the like can further be added to the culture liquid.

The mesenchymal stem cells seeded in the culture liquid in which the material for the undifferentiated state-maintaining culture is dispersed can be cultured usually at 10° C. to 40° C., preferably 35° C. to 38° C., for example, 37° C.; in the carbon dioxide atmosphere of 0% by volume to 10% by volume, preferably 3% by volume to 7% by volume, for example, 5% by volume; in an incubator for cell cultures.

If necessary, the culture liquid may be replaced during culturing of the cells in order to keep the culture environment fresh. For example, in the case where nanofibers are used as the material for the undifferentiated state-mamtainine culture, the replacement of the culture liquid can be conducted by precipitating and collecting both of nanofibers and cells dispersed in the cell culture liquid by centrifugation under a predetermined centrifugal force condition, and re-dispersing them in a fresh culture liquid.

For example, by culturing somatic stem cells such as mesenchymal stem cells with the above-described procedure under a culture condition of 37° C. and 5% by volume carbon dioxide atmosphere by using the material for maintaining the undifferentiated state of the present invention, an undifferentiated state and multipotency of the somatic stem cells cultured for 1 day to 30 days can be maintained at comparable degrees to an undifferentiated state and multipotency of the somatic stem cells immediately after collection.

[Harvest Method]

When somatic stem cells are cultured under the culture condition in which the material for maintaining the undifferentiated state of the present invention is used, the somatic stem cells can be harvested by a treatment with trypsin.

By using the material for the undifferentiated state-maintaining culture of the present invention, the undifferentiated state and differentiation potential can be maintained, and cell senescence can also be suppressed for somatic stem cells such as mesenchymal stem cells, even when 2 weeks or more, for example, 30 days have passed after beginning of the resting culture of these cells.

EXAMPLES

Hereinafter, the characteristics of the present invention will be explained more specifically with Examples. The materials, amounts used, percentages of uses, treatment details, and treatment procedures shown in the following Examples may suitably be changed, as long as not departing from the scope of the present invention. Accordingly, the scope of the present invention should not be construed as limited by the specific examples described below.

[Measurement of Average Particle Size "d"]

According to the procedure described in [0026], an average particle size "d" of the cellulose nanofibers obtained in each of Production Examples 1 to 3 below was determined by measuring dynamic light scattering.

[Measurement of Average Fiber Diameter "D" and Average Fiber Length "L"]

According to the procedure described in [0026], an average fiber diameter "D" and an average fiber length "L" of the cellulose nanofibers obtained in each of Production Examples 1 to 3 below were determined from the TEM image and SEM image, and an aspect ratio L/D was calculated from these values.

Production Example 1

Production of Microcrystalline Cellulose-Derived Cellulose Nanofiber (MC1)

1,000 parts by mass of pure water was added to 1.5 parts by mass of the commercially available microcrystalline cellulose (Funacel powder II for column chromatography, manufactured by Funakoshi Co., Ltd.) to allow the microcrystalline cellulose dispersed, and a pulverization treatment was then performed at 245 MPa for 50 times by using the high pulverization device manufactured by Sugino Machine Limited (Star Bunt system) to obtain an aqueous dispersion liquid of cellulose nanofibers derived from microcrystalline cellulose (MC1).

Production Example 2

Production of Microcrystalline Cellulose-Derived Cellulose Nanofiber (MC2)

1,000 parts by mass of pure water was added to 15 parts by mass of the commercially available microcrystalline cellulose (Funacel powder II for column chromatography, manufactured by Funakoshi Co., Ltd.) to allow the microcrystalline cellulose dispersed, and a pulverization treatment was then performed at 245 MPa for 150 times by using the high-pressure pulverization device manufactured by Sugino Machine Limited (Star Burst system) to obtain an aqueous dispersion liquid of cellulose nanofibers derived from microcrystalline cellulose (MC2).

Production Example 3

Production of Microcrystalline Cellulose-Derived Cellulose Nanofiber (MC3)

1,000 parts by mass of pure water was added to 15 parts by mass of the commercially available microcrystalline cellulose (Funacel powder II for column chromatography, manufactured by Funakoshi Co., Ltd.) to allow the microcrystalline cellulose dispersed, and a pulverization treatment was then performed at 245 MPa for 300 times by using the high-pressure pulverization device manufactured by Sugino Machine Limited (Star Burst system) to obtain an aqueous dispersion liquid of cellulose nanofibers derived from microcrystalline cellulose (MC3).

Production Example 4

Production of Pulp-Derived Cellulose Nanofiber (PC)

978 parts by mass of pure water was added to 22 parts by mass of the commercially available kraft pulp (LBKP D-8, manufactured by KOKUSAI PULP & PAPER Co., Ltd., the solid content is 46% by mass) to allow the pulp dispersed, and a pulverization treatment was then performed at 245 MPa for 200 times by using the high-pressure pulverization device manufactured by Sugino Machine Limited (Star Burst system) to obtain an aqueous dispersion liquid of cellulose nanofibers derived from pulp. The obtained dispersion liquid was weighed and placed in a dish, dried at 110° C. for 1 hour to remove water, and an amount of the residue was measured to determine the concentration. As a result, the cellulose concentration in water (the concentration of solid content) was 1.0% by mass. The dispersion liquid was diluted with pure water to be 10 times by mass, and thus the 0.1% by mass aqueous dispersion liquid (PC) was obtained.

Production Example 5

Production of Bacterial Cellulose-Derived Cellulose Nanofiber (BC)

200 parts by mass of commercially available bacterial cellulose (manufactured by UTAMA, PT, NIRAMAS, and the solid content of cellulose in the acetic acid aqueous solution is about 0.5% by mass) was crashed in a household blender for 5 minutes. The obtained slurry was filtrated, and was dispersed in pure water. Then, pH was measured, and such a washing process was repeated until the pH became neutral (6 to 7). Pure water was added so that the total volume became 1,000 parts by mass, and a pulverization treatment was then performed at 200 MPa for 300 times by using the high-pressure pulverization device manufactured by Sugino Machine Limited (Star Burst system) to obtain an aqueous dispersion liquid of cellulose nanofibers derived from bacterial cellulose (BC).

For the cellulose nanofibers obtained in Production Examples 1 to 5, average particle sizes "d", average fiber diameters "D," and average fiber lengths "L" were measured according to the aforementioned procedure. The obtained results and aspect ratios (L/D) calculated from average fiber diameters "D" and average fiber lengths "L" are shown.

TABLE 1

|  | Average Particle Size d [nm] | Average Fiber Diameter D [nm] | Average Fiber Length L [nm] | Aspect Ratio L/D |
|---|---|---|---|---|
| Production Example 1 (MC1) | 240 | 20.1 | 189 | 9.4 |
| Production Example 2 (MC2) | 150 | 19.9 | 172 | 8.6 |
| Production Example 3 (MC3) | 110 | 19.8 | 169 | 8.5 |
| Production Example 4 (PC) | 650 | 17.7 | 3,540 | 200 |
| Production Example 5 (BC) | 320 | 22.8 | 2,540 | 111 |

Example 1 hMSC Culture using MC1

[Preparation of Culture Liquid]

To 100 mL of the 0.1% by mass aqueous dispersion liquid of cellulose nanofibers (MC1) obtained in Production Example 1, the commercially available powder medium that can be subjected to high pressure steam sterilization (Dulbecco's Modified Eagle's Medium 2, manufactured by Nissui Pharmaceutical Co., Ltd.) was added in the amount for 100 mL. The mixture was stirred for about 30 minutes with a magnetic stirrer to dissolve the powder medium in the aqueous dispersion liquid, and was then subjected to high pressure steam sterilization at 121° C. for 15 minutes. The solution was cooled to a room temperature, and the commercially available glutamine solution (200 mmol/L L-glutamine solution (×100) manufactured by Wake Pure Chemical Industries, Ltd.) was added thereto so that the final concentration became 2 mM, and then 1 mL of a 10% by mass sterilized sodium bicarbonate aqueous solution was further added. A small portion taken out from the solution was tested with a pH test paper to confirm that the pH of the solution was about 70 to 8.0. Before use, a fetal bovine serum (hereinafter, abbreviated as FBS) was added to the solution to be 10% by volume, and thus 0.1% (w/v) MC1 culture liquid was prepared. Depending on purposes, the DMEM medium (Gibco (registered trademark) DMEM, Powder, Low Glucose, Pyruvate 31600-034) containing 10% by volume of FBS was further mixed in the MC1 culture liquid in order to adjust the cellulose nanofiber concentration in the culture liquid (see the NF concentrations in Table 2 and FIGS. 1 to 4).

[Seeding of Mesenchymal Stem Cell MSC]

To the 10 cm-diameter low-adhesion ASNOL sterilized dish (manufactured by AS ONE Corporation, GD90-15) that is a non-hydrophilized polystyrene dish, 10 mL of a 0.025% (w/v) to 0.1% (w/v) MC1 culture liquid was added as a medium, and 5.0×10⁵/dish human mesenchymal stem cells (Lonza PT-2501; hereinafter, abbreviated as hMSC) were seeded therein. The seeded cells were cultured for 1 day at 37° C., in 5% by volume carbon dioxide, and the culture liquid was transferred to a new ASNOL sterilized dish in order to remove adhering cells adhering on the dish, and the culture was further continued for 4 weeks. During the culture, the medium was exchanged every 1 week as follows. The culture liquid was collected in a centrifuge tube, and centrifuged at 10° C., 300 g for 5 minutes to remove supernatant. Then precipitate was resuspended in 10 mL of fresh DMEM medium containing 10% by volume PBS, and was transferred to a new ASNOL sterilized dish.

The culture liquid was collected at each time point of 1 week to 4 weeks after beginning of the culture, and a viability determination of the cells by a calcein-AM/PI method, harvest of the cells by a treatment with trypsin, and immunostaining of undifferentiation markers were performed according to the procedures below.

<Viability Determination by Calcein-AM/PI Method>

From each of the culture liquids collected 1 week to 4 weeks after beginning of the culture, 0.5 mL was taken, and was centrifuged at 10° C., 300 g for 5 minutes to remove supernatant. Precipitate of nanofibers (hereinafter, referred to as NF) was washed with 1 mL of phosphate buffer (hereinafter, referred to as PBS). The washing was repeated 2 times, and 0.5 mL of a calcein-AM/PI solution was added to the NF precipitate, and mixed. Then, the mixture was incubated at 37° C., in 5% by volume carbon dioxide for 30 minutes. Next, the NF precipitate was washed 2 times with PBS, and then 0.5 mL of DMEM medium was added to suspend the NF precipitate. The suspension was transferred to a 24-well plate, and the plate was subjected to phase-contrast microscopy and fluorescent microscopy. Under the fluorescent microscopy, green fluorescence (living cells) and red fluorescence (dead cells) were confirmed. The obtained results are shown in FIGS. 1 and 2.

<Cell Harvest by Treatment with Trypsin>

Each of the culture liquids collected from one dish after 1 week to 4 week cultures was transferred to a centrifuge tube, and centrifuged at 10° C. 300 g for 5 minutes to separate supernatant and precipitate. The precipitate was washed 2 times with 10 mL of PBS, and the obtained supernatant was also collected. All supernatants were centrifuged at 10° C., 430 g for 3 minutes to obtain precipitate. All precipitates obtained were combined, and the trypsin solution (0.25% (w/v) Trypsin-1 mmol/l EDTA-4Na Solution with Phenol Red, manufactured by Wako Pure Chemical Industries, Ltd.) was added thereto in an amount about equal to that of the precipitate, and incubated at 37° C. for 5 minutes. After that, a DMEM medium containing 10% by volume FBS was added thereto in an amount twice of that of the trypsin solution and mixed, and then the mixture was centrifuged at 10° C., 300 g for 5 minutes to separate supernatant and precipitate. The supernatant was further centrifuged at 10° C., 430 g for 3 minutes, and the obtained supernatant was removed. The obtained precipitate and the precipitate separated earlier were combined, and suspended in 10 mL of a fresh DMEM medium containing 10% by volume FBS, and then reseeded in a hydrophilized cell culture polystyrene dish (Tissue culture polystyrene, hereinafter, abbreviated as TCPS) having the diameter of 10 cm. After incubating the reseeded cells at 37° C., in 5% by volume carbon dioxide overnight, cells adhering on the dish were observed. The adhering cells were treated with the trypsin solution same as the above, and incubated at 37° C. for 5 minutes, and then the DMEM medium containing 10% by volume FBS was added thereto in an amount twice or above of that of the trypsin solution to a maximum amount, and in an additional amount of about 10 mL, and mixed, and then the mixture was centrifuged at 10° C., 430 g for 3 minutes. The obtained precipitated cells were suspended in several milliliters of a fresh DMEM medium containing 10% by volume FBS. The suspension was measured by using a hematocytometer.

As an object to be compared, hMSCs in a DMEM medium containing 10% by volume FBS were also seeded in a TCPS having the diameter of 10 cm at $5.0 \times 10^5$/dish at the time of seeding, and the cells were collected and counted on the next day of seeding. The number of the cells referred to 100% recovery, and was used to calculate recovery rate of the cells subjected to the aforementioned culture. The obtained results are shown in Table 2 below. Because it is difficult to count suspended cells directly, a percentage of the cells attached to the material for maintaining the undifferentiated state was calculated as follows. On the next day of the culture with the nanofiber dispersion liquid, cells precipitated and attached to a culture dish without attaching to dispersed nanofibers were collected by the treatment with trypsin, and counted. The number of the cells was subtracted from the number of the cells to be compared, and thus the percentage of cell-attachment was obtained.

[Confirmation of Resting State]

To evaluate whether mesenchymal stem cells were cultured in a resting condition while keeping the characteristics thereof, expressions of various marker proteins that characterize mesenchymal stem cells were observed and evaluated.

After culturing for 1 week to 4 weeks, cells harvested by a treatment with trypsin from MC1 of Example 1 were seeded in a 24-well plate at $5.0 \times 10^3/cm^2$ ($9.5 \times 10^3$/well), and incubated at 37° C., in 5% by volume carbon dioxide overnight.

The cells were subjected to immunofluorescent staining with marker antibodies against human mesenchymal stem cells (6 antibodies were for positive markers, and 5 antibodies were for negative markers) to evaluate if the cells were in a resting state. The immunofluorescent staining was performed as follows. Cells were washed with PBS, and fixed with a 4% paraformaldehyde-phosphate buffer. After washing, the cells were treated for blocking with PBS containing 1% (w/v) bovine serum albumin and 10% by volume donkey serum (blocking buffer). The treated cells were reacted with suitably diluted mouse monoclonal antibodies at 4° C. overnight. After washing to remove primary antibodies, the cells were reacted with fluorescein isothiocyanate (FITC)-labelled anti-mouse antibodies at a room temperature for 1 hour. After washing, whether the labelled cells emit green fluorescence under fluorescent microscopy (positivity and expression intensity) was confirmed. The immunostaining results after culturing 4 weeks are shown in FIGS. 3 and 4.

As a control test, hMSCs, which were passaged 6 times same as the cells used in Examples 1 to 3, were cultured under the same seeding condition as those in the cases of Examples, and subjected to immunofluorescent staining with marker antibodies.

Example 2

Culture of hMSC using MC2

By using a 0.1% by mass aqueous dispersion liquid of cellulose nanofibers obtained in Production Example 2 (MC2), a 0.1% (w/v) MC2 culture liquid was prepared by preparing a medium according to the same method as that in the case of Example 1. Then, hMSCs were seeded and cultured in the prepared culture liquid according to the same method as that in the case of Example 1. After culturing for 1 week to 4 weeks, the cells were subjected to viability determination by the calcein-AM/PI method, cell harvest with trypsin, and confirmation of a resting state.

Example 3

Culture of hMSC using MC3

By using a 0.1% by mass aqueous dispersion liquid of cellulose nanofibers obtained in Production Example 3 (MC3), a 0.1% (w/v) MC3 culture liquid was prepared by preparing a medium according to the same method as that in the case of Example 1. Then, hMSCs were subjected to a long-term culture in the prepared culture liquid conducted according to the same method as that in the case of Example 1, and were subjected to viability determination by the calcein-AM/PI method, cell harvest, and confirmation of a resting state.

Example 4

Culture of hMSC using PC

By using a 0.1% by mass aqueous dispersion liquid of cellulose nanofibers obtained in Production Example 4 (PC), a 0.1% (w/v) PC culture liquid was prepared by preparing a medium according to the same method as that in the case of Example 1. TCPS was used for culturing hMSCs, and cells were subjected to viability determination and cell harvest with trypsin. In Example 4, cells were harvested also on the next day of the culture.

Example 5

Culture of hMSC using BC

By using a 0.1% by mass aqueous dispersion liquid of cellulose nanofibers obtained in Production Example 5 (BC), a 0.1% (w/v) PC culture liquid was prepared by preparing a medium according to the same method as that in the case of Example 1. TCPS was used for culturing hMSCs, and cells were subjected to viability determination and cell harvest with trypsin.

Example 6

Culture of hMSC using Methylcellulose

By using methylcellulose (M0387, manufactured by Aldrich Chemical Co., Inc.: ME), a 1.0% by mass aqueous dispersion liquid was prepared, and by using the dispersion liquid, a 1.0% (w/v) methylcellulose culture liquid was prepared by preparing a medium according to the same method as that in the case of Example 1. The ASNOL sterilized dish was used for culturing hMSCs, and cells were subjected to viability determination and cell harvest with trypsin. In Example 6, cells were harvested also on three days after the culture.

Example 7

Culture of hMSC using Diutan Gum

By using a 1.0% by mass aqueous dispersion liquid of diutan gum (KELCO CRETE DG-F, manufactured by SANSHO Co., Ltd.: DU), a 1.0% (w/v) diutan gum culture liquid was prepared by preparing a medium according to the same method as that in the case of Example 1. The ASNOL sterilized dish was used for culturing hMSCs, and cells were subjected to viability determination and cell harvest with trypsin. In Example 7, cells were harvested also on three days after the culture.

[Result: Determination of Cell Viability]

As shown in FIGS. 1 and 2, in all of the cases in Examples 1 to 3, a calcein-AM staining image of living cells (green fluorescence) was still observed after 4 weeks; however, PI-stained cells representing dead cells (red fluorescence) were infrequently observed. That is, these observation results show that hMSCs can be cultured for 4 weeks or more by using the MC1 to MC3 nanofiber-dispersed culture liquids. Also in Examples 4 and 5, calcein-AM staining images were observed after 1 week, which showed that hMSCs can be cultured also by PC and BC nanofiber-dispersed culture liquids.

In Examples 1 and 2, from a few cells to around ten cells were obviously aggregated during the culture. In Example 3, however, living cells were well dispersed after 4 weeks had passed, which suggests that especially the MC3 nanofiber-dispersed culture liquid provides a homogeneous culture environment to each of the stem cells.

[Result: Cell Recovery Rate]

As shown in Table 2, in all of the cases in Examples 1 to 5, attachment of the material for the undifferentiated state-maintaining culture to cells were confirmed on the next day of seeding, and in particular, over 80% of cell attachment was confirmed in each of Examples 1 to 3, and 5. As it will be mentioned later, because cells can be harvested after certain culture periods in Examples 6 (methylcellulose) and 7 (diutan gum), it can be said that a material for an undifferentiated state-maintaining culture is attached to cells on the next day of seeding also in these Examples.

In Examples 1 to 3, about 40% to 60% of cells can be harvested after 4 weeks. In particular, the highest recovery rate was obtained in a culture using MC1 in Example 1, and 61.2% of cells can be harvested after the long-term, that is, 4 week culture.

It was also confirmed that, in Examples 4, 6, and 7, cells can be harvested after certain culture periods.

From these results, it is understood that both of the nanofiber-dispersed culture liquid and polysaccharide thickener-dispersed culture liquid are effective for readhesion of hMSCs after harvest and reseeding thereof. In particular, it is understood that in Examples 1 to 3, in which aqueous dispersion liquids of nanofibers derived from the same microcrystalline cellulose (MC1 to MC3) were used, cell recover rates were improved when the lengths of nanofibers were long. Above all, it is understood that a solution in which nanofibers derived from microcrystalline cellulose were dispersed is effective for readhesion of hMSCs after harvest and reseeding thereof.

TABLE 2

|  | Concentration* | Cell Attachment Rate %*[1] (Next Day of Seeding) | Cell Recovery Rate % in Each Culture Period |  |  |  |  |  |
|---|---|---|---|---|---|---|---|---|
|  |  |  | 1 Day | 3 Days | 1 Week | 2 Weeks | 3 Weeks | 4 Weeks |
| Example 1 MC1 | 0.025% 0.05% | 87.4 98.1 | — — | — — | 47.0 42.0 | 58.8 52.7 | — — | 61.2 44.8 |
| Example 2 MC2 | 0.025% 0.05% | 88.6 95.6 | — — | — — | 39.4 40.2 | 56.1 41.9 | — — | 38.0 39.7 |
| Example 3 MC3 | 0.05% | 86.3 | — | — | — | — | 40.0 | 46.0 |
| Example 4 PC | 0.1% | 43.8*[2] | 16.9*[2] | — | — | — | — | — |
| Example 5 BC | 0.1% | 80.3*[2] | — | — | — | — | — | — |
| Example 6 ME | 0.5% | — | — | — | 21.9*[3] | — | — | — |
| Example 7 DU | 0.05% 0.1% 0.2% | — — — | — — — | 9.3 18.2 56.1 | — — 43.7*[3] | — — 24.5*[3] | — — — | — — — |

*A concentration of cellulose nanofibers or polysaccharide thickeners in a culture liquid (% (w/v)).
*[1]Cell attachment rate (%) to the material for maintaining the undifferentiated state.
*[2]TCPS (a cell culture polystyrene dish) was used for culturing hMSC.
*[3]Harvested cells were defective for adhesion and extension, and included dead cells.

[Result: Confirmation of Resting State]

As shown in Table 3, on 4 weeks after the culture using a nanofiber-dispersed culture liquid, all of the cells in Examples 1 to 3 showed normal expressions of STRO-1, CD29, CD44, CD73, CD90, and CD105 as positive markers with comparable degrees to those in a control test.

As shown in FIG. 4, these cells showed immunostaining fluorescent intensities of CD11b, CD14, CD19, CD34, and CD45 as negative markers with comparable degrees to those in a control test, and thus it was confirmed that these cells almost normally maintain characteristics of hMSCs after 4 weeks of the culture.

Examples 8 to 10

MSC Culture on Non-Adherent Cell Culture Dish using MC1

[Preparation of Culture Liquid]

A culture liquid was prepared according to the same condition and procedure as those in the case of Example 1.

[Seeding of Mesenchymal Stem Cell MSC]

To the 10 cm-diameter non-adherent cell culture dish (CellStar 664970, manufactured by Greiner Bio-One International GmbH), 10 mL of a 0.02% by mass, 0.017% by mass, or 0.0125% by mass MC1 culture liquid was added as a medium, and $5.0 \times 10^5$/dish hMSCs were seeded therein. The medium was exchanged every 1 week as follows. The culture liquid was collected in a centrifuge tube, and centrifuged at 10° C., 300 g for 5 minutes to remove supernatant. Then precipitate was resuspended in 10 mL of fresh DMEM medium containing 10% by mass FBS, and was brought back to the original non-adherent cell culture dish. The culture liquid was collected at each time point of 1 week to 4 weeks after beginning of the culture, and a viability determination of the cells by a calcein-AM/PI method, harvest of the cells by a treatment with trypsin, and immunostaining of undifferentiation markers of cells were performed according to the procedures described in paragraphs [0046], [0047], and [0048].

[Confirmation of Maintained Multipotency]

To confirm whether harvested cells were cultured in a resting condition while maintaining multipotency, differentiation induction to adipocytes, osteocytes, and chondrocytes were performed by using the commercially available differentiation inducing medium (Human mesenchymal stem cell functional identification kit, sc006, manufactured by R&D Systems, Inc.). The differentiated cells were immunostained with marker antibodies to confirm whether these cells possess differentiation potential to each of the cell lineages.

<Culture in MC1 Medium and Cell Harvest>

After culturing hMSCs in a 0.02% MC1 culture liquid, for 2 weeks, cells were harvested by treating with trypsin according to the procedure described in the paragraph [0047].

<Induction of Differentiation to Adipocyte> hMSCs harvested from the MC1 medium were resuspended in a basal medium in which 10% FBS, penicillin-streptomycin, and glutamine were added to αMEM (MEMα 12560-056, manufactured by Life Technologies Corporation), and then reseeded in a 24-well plate having a sterilized cover glass at $2.1 \times 10^4/cm^2$. The cells were cultured until becoming 100% confluent, and then the medium was replaced with a basal medium containing a differentiation inducing agent to adipocytes. The medium containing the differentiation inducing agent was replaced to the fresh one every 3 days or 4 days, and the culture was continued for 3 weeks. The cover glass was taken out 1 week to 3 weeks after the culture, and the cultured hMSCs were immunostained by oil red O-staining and by using an anti-FABP4 antibody.

<Induction of Differentiation to Osteocyte>

To prevent cell detachment during induction of differentiation to osteocytes, an 1 μg/mL fibronectin solution was added to a 24-well plate having a sterilized cover glass, and the plate was treated at 37° C. for 3 hours to 30 hours. hMSCs harvested from the MC1 medium were resuspended in a basal medium in which 10% FBS, penicillin-streptomycin, and glutamine were added to αMEM (MEMα 12560-056, manufactured by Life Technologies Corporation), and then reseeded in the prepared 24-well plate at $4.2 \times 10^3/cm^2$. After overnight culture, the medium was replaced with a basal medium containing a differentiation inducing agent to osteocytes. The medium containing the differentiation inducing agent was replaced to the fresh one every 3 days or 4 days, and the culture was continued for 4 weeks. The cover glass was taken out 2 weeks to 4 weeks after the culture, and the cultured cells were subjected to alizarin red S-staining.

<Induction of Differentiation to Chondrocyte> hMSCs harvested from the MC1 medium were adjusted to $1.0 \times 10^6/mL$ with DMEM(FBS-). In order to form cell aggregations, 10 μL (10,000 cells) of the adjusted MC1 medium was added to a suitable amount of 3% methylcellulose/DMEM placed in TCPS. After overnight culture, cell aggregations were taken out by a flame-sterilized spatula, and washed with PBS, and then transferred to the chamber slide system (Lab-Tek Chamber Slide System 178599JP, manufactured by Nunc) as one cell aggregation per each well. 100 μL of a basal medium, in which the ITS Supplement (the accessory of sc006), penicillin-streptomycin, and glutamine were added to DMEM/F-12 (DMEM/F-12 11320-033, manufactured by Life Technologies Corporation), and to which a differentiation inducing agent to chondrocytes was further added, was added to each well. The medium was exchanged every 2 days to 3 days, and the culture was continued for 4 weeks. The cells were immunostained with an anti-aggrecan antibody 3 weeks or 4 weeks after the culture.

Production Example 6

Production of Microcrystalline Cellulose-Derived Cellulose Nanofiber (MC4)

1,000 parts by mass of pure water was added to 1.5 parts by mass of the commercially available microcrystalline cellulose (CEOLUS, PH-101, manufactured by Asahi Kasei Chemicals Corporation) to allow the microcrystalline cellulose dispersed, and a pulverization treatment was then performed at 220 MPa for 50 times by using the high-pressure pulverization device manufactured by Sugino Machine Limited (Star Burst system) to obtain an aqueous dispersion liquid of cellulose nanofibers derived from microcrystalline cellulose (MC4).

Production Example 7

Production of Microcrystalline Cellulose-Derived Cellulose Nanofiber (MC5)

1,000 parts by mass of pure water was added to 1.5 parts by mass of the commercially available microcrystalline cellulose (CEOLUS, PH-101, manufactured by Asahi Kasei Chemicals Corporation) to allow the microcrystalline cellulose dispersed, and a pulverization treatment was performed at 220 MPa for 100 times by using the high-pressure pulverization device manufactured by Sugino Machine Limited (Star Burst system) to obtain an aqueous dispersion liquid of cellulose nanofibers derived from microcrystalline cellulose (MC5).

Production Example 8

Manufacture of Microcrystalline Cellulose-Derived Cellulose Nanofiber (MC6)

1,000 parts by mass of pure water was added to 1.5 parts by mass of the commercially available microcrystalline cellulose (CEOLUS, PH-101, manufactured by Asahi Kasei Chemicals Corporation) to allow the microcrystalline cellulose dispersed, and a pulverization treatment was performed at 220 MPa for 150 times by using the high-pressure pulverization device manufactured by Sugino Machine Limited (Star Burst system) to obtain an aqueous dispersion liquid of cellulose nanofibers derived from microcrystalline cellulose (MC6).

For the cellulose nanofibers obtained in Production Examples 6 to 8, average fiber diameters "D" and average fiber lengths "L" were measured according to the aforementioned procedure. The obtained results and aspect ratios (L/D) calculated from average fiber diameters "D" and average fiber lengths "L" are shown.

TABLE 3

|  | Average Fiber Diameter D [nm] | Average Fiber Length L [nm] | Aspect Ratio L/D |
|---|---|---|---|
| Production Example 6 (MC4) | 19 | 270 | 14.2 |
| Production Example 7 (MC5) | 13 | 178 | 13.7 |

[Preparation of DMEM Culture Liquid having Twofold Concentration]

To 50 mL of ultrapure water, the commercially available powder medium that can be subjected to high pressure steam sterilization (Dulbecco's Modified Eagle's Medium 2, manufactured by Nissui Pharmaceutical Co., Ltd.) was added in the amount for 100 mL. The mixture was stirred for about 30 minutes with a magnetic stirrer to dissolve the powder medium in the aqueous dispersion liquid, and was then subjected to high pressure steam sterilization at 121° C. for 15 minutes. The solution was cooled to a room temperature, and the commercially available L-glutamine solution (200 mmol/L L-glutamine solution (×100) manufactured by Wako Pure Chemical Industries, Ltd.) was added thereto so that the final concentration became 4 mM, and then 1 mL of a 10% by mass sterilized sodium bicarbonate aqueous solution was further added to prepare DMEM having twofold concentration. A small portion taken out from the solution was tested with a pH test paper to confirm that the pH of the solution was about 7.0 to 8.0.

Example 11

Culture of hMSC using MC4

To a 0.1% by mass steam-sterilized aqueous dispersion liquid of cellulose nanofibers (MC4) obtained in Production Example 6, an equal amount of sterilized DMEM having twofold concentration (penicillin-streptomycin also has twofold concentration) was mixed to prepare a 0.05% culture liquid. Then, FBS was added to the culture liquid to be 10% FBS. hMSCs were seeded in a low-adhesion ASNOL dish (manufactured by AS ONE Corporation), and cultured according to the same method as that in the case of Example 1. The cells were harvested, and immunostained with undifferentiation markers.

Example 12

Culture of hMSC using MC5

To a 0.1% by mass steam-sterilized aqueous dispersion liquid of cellulose nanofibers (MC5) obtained in Production Example 7, an equal amount of sterilized DMEM having twofold concentration (penicillin-streptomycin also has twofold concentration) was mixed to prepare a 0.05% culture liquid. Then, FBS was added to the culture liquid to be 10% FBS. hMSCs were seeded in a low-adhesion ASNOL dish, and cultured according to the same method as that in the case of Example 1. The cells were harvested, and immunostained with undifferentiation markers.

Example 13

Culture of hMSC using MC6

To a 0.1% by mass steam-sterilized aqueous dispersion liquid of cellulose nanofibers (MC6) obtained in Production Example 8, an equal amount of sterilized DMEM having twofold (penicillin-streptomycin also has twofold concentration) was mixed to prepare a 0.05% culture liquid. Then, FBS was added to the culture liquid to be 10% FBS. hMSCs were seeded in a low-adhesion ASNOL dish, and cultured according to the same method as that in the case of Example 1. The cells were harvested, and immunostained with undifferentiation markers.

[Control Test: Culture of hMSC using DMEM]

As a control test, hMSC was seeded in a low-adhesion ASNOL dish with DMEM (containing 10% FBS), and cultured. Viability of the cells were determined, and the cells were harvested by centrifuging the medium.

[Result: Cell Recovery Rate]

In Table 4, cell attachment rates and cell recovery rates of Examples 8 to 13, and of a hMSC culture using DMEM (without NF) (control test) are shown.

As shown in Table 4, in the culture using 0.02% by mass MC1 of Example 8, 83.4% of the cells were recovered after 4 weeks of the culture, when a non-adherent cell culture dish was used. In Examples 9 and 10, although cells were cultured using MC1 having a low concentration, that is, 0.017% or 0.0125%, higher cell recovery rates of 60% to 80% were obtained.

For the series of MC4 to MC6, which are in industrial scales, cell recovery rates until after 2 weeks of cultures were only around 40% when cells were cultured using MC4 of Example 11 or MC6 of Example 13. In this series, the highest cell recovery rate was obtained when cells were cultured using MC5 of Example 12, that is, 72% and 53% of cell recovery rates were obtained after 2 weeks and 4 weeks of the culture, respectively.

It is understood from these results that solutions in which nanofibers derived from microcrystalline cellulose of Examples 1 to 3 and Examples 8 to 13 were dispersed, are particularly effective for recovery of hMSC and readhesion of hMSCs after reseeding thereof.

TABLE 4

|  | NF Concentration | Cell Attachment Rate %*[1] (Next Day of Seeding) | Cell Recovery Rate % in Each Culture Period | | |
|---|---|---|---|---|---|
|  |  |  | 1 Week | 2 Weeks | 4 Weeks |
| Example 8 MC1 | 0.02% | 100 | 63.6 | 63.3 | 83.4 |
| Example 9 MC1 | 0.017% | 100 | 80.6 | 81.5 | 70.5 |
| Example 10 MC1 | 0.0125% | 100 | 63.9 | 70.1 | 63.0 |

TABLE 4-continued

| | NF Concentration | Cell Attachment Rate %*[1] (Next Day of Seeding) | Cell Recovery Rate % in Each Culture Period | | |
|---|---|---|---|---|---|
| | | | 1 Week | 2 Weeks | 4 Weeks |
| Example 11 MC4 | 0.02% | 100 | 60.8 | 40.5 | 44.4 |
| Example 12 MC5 | 0.02% | 100 | 58.1 | 71.9 | 53.5 |
| Example 13 MC6 | 0.02% | 100 | 54.6 | 40.0 | — |
| Control Test DMEM | 0 | 100 | 34.0 | — | — |

[Result: Confirmation of Resting State]

As shown in Table 6, on 4 weeks after the dispersing culture using MC5 of Example 12 that is in an industrial scale, the cells showed normal expressions of STRO-1, CD29, CD44, CD73, CD90, and CD105 as positive markers with comparable degrees to those in a control test.

As shown in FIG. 7, these cells showed immunostaining fluorescent intensities of CD11b, CD14, CD19, CD34, and CD45 as negative markers with comparable degrees to those in a control test, and thus it was confirmed that these cells almost normally maintain characteristics of hMSCs after 4 weeks of the culture.

[Result: Confirmation of Differentiation Inducing Potential]

For Example 8, which represents the highest cell recovery, to confirm whether hMSCs harvested after a dispersing culture maintain multipotency, each of differentiation potentials to the three directions, which are regarded as standards of stem cell characteristics maintained by MSC, that is, differentiation potentials to adipocytes, osteocytes, and chondrocytes were tested, according to the same method as described in paragraphs [0061] to [0063].

After adipocyte differentiation test was conducted for hMSCs cultured in Example 8, an immunostaining test using an anti-FABP4 antibody and oil red O-staining were conducted to the hMSCs. The results are shown in FIG. 8 (anti-FABP4 immunostaining test) and FIG. 9 (oil red O-staining).

Figure 9:
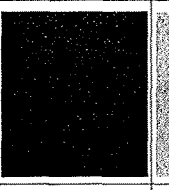
FIG. 9 is a figure showing results of oil red O-staining of hMSCs that were cultured in Example 8, and were then subjected to an adipocyte differentiation inducing test.

As shown in FIG. 8, hMSCs that were harvested and subjected to adipocyte differentiation induction showed significant expression of FABP4, and accumulation of lipid droplet was also observed as shown in FIG. 9 (oil red O-staining). With these results, it was confirmed that the adipocyte differentiation potential was maintained in hMSCs after the dispersing culture.

Figure 10:
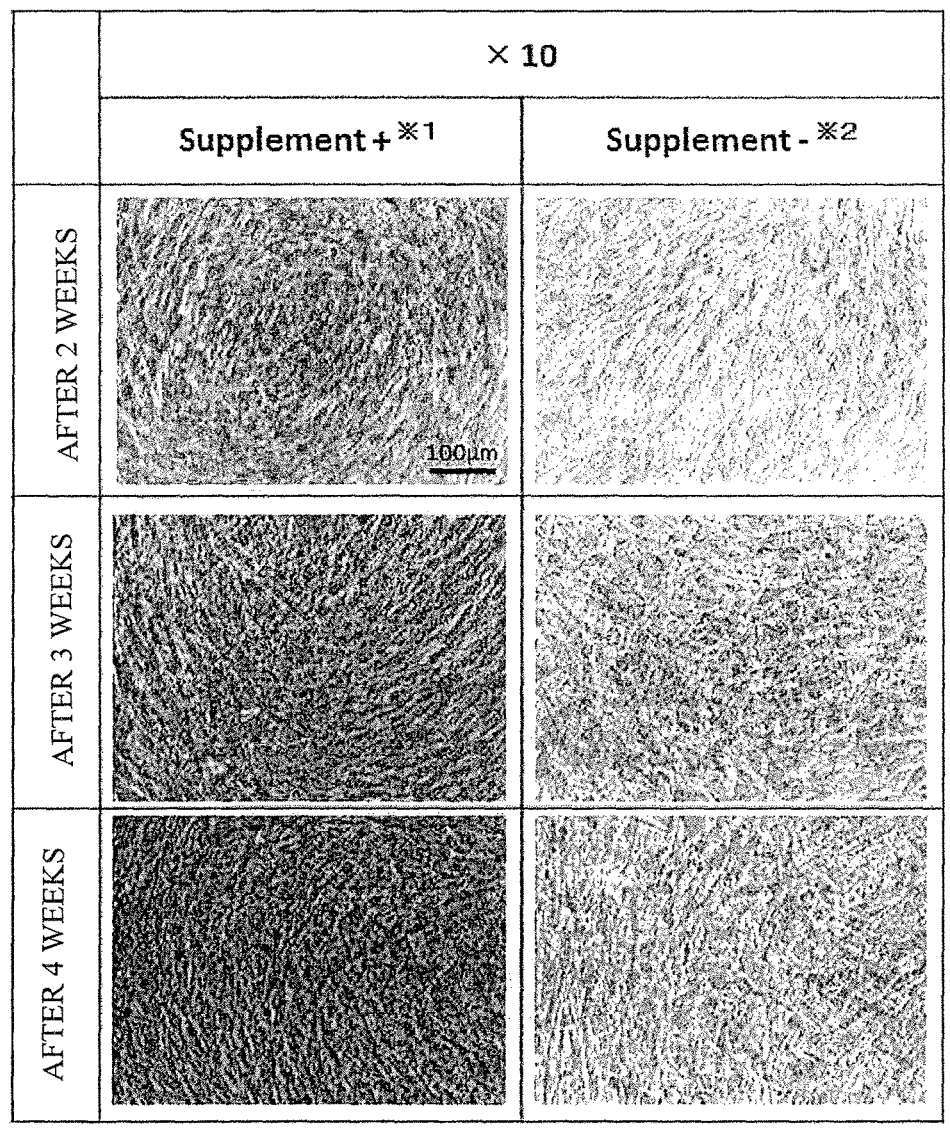
FIG. 10 is a figure showing results of alizarin red S-staining tests of hMSCs that were cultured in Example 8, and were then subjected to an osteocyte differentiation inducing test.

Also, the result of alizarin red S staining of hMSCs that were cultured in Example 8, and subjected to the osteocyte differentiation test are shown (see, FIG. 10).

As shown in FIG. 10, hMSCs subjected to osteocyte differentiation induction were significantly stained with alizarin red, and thus it was confirmed that the osteocyte differentiation inducing potential was maintained in hMSCs after the dispersing culture.

Figure 11:
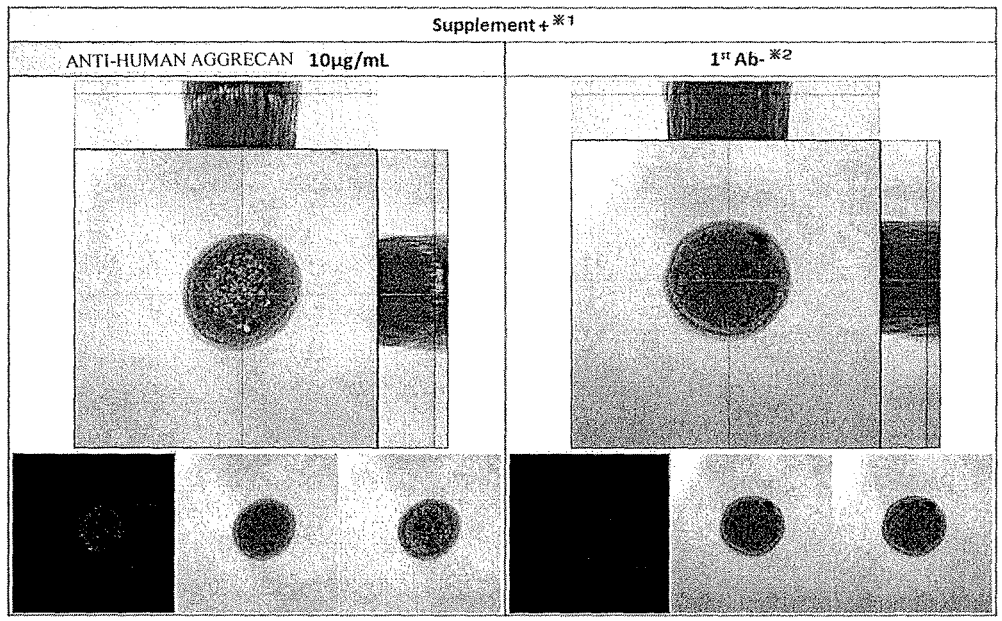
FIG. 11 is a figure showing results of immunostaining tests of hMSCs by using an anti-aggrecan antibody. The hMSCs were cultured in Example 8, and were then subjected to a chondrocyte differentiation inducing test for 3 weeks.
Figure 12:
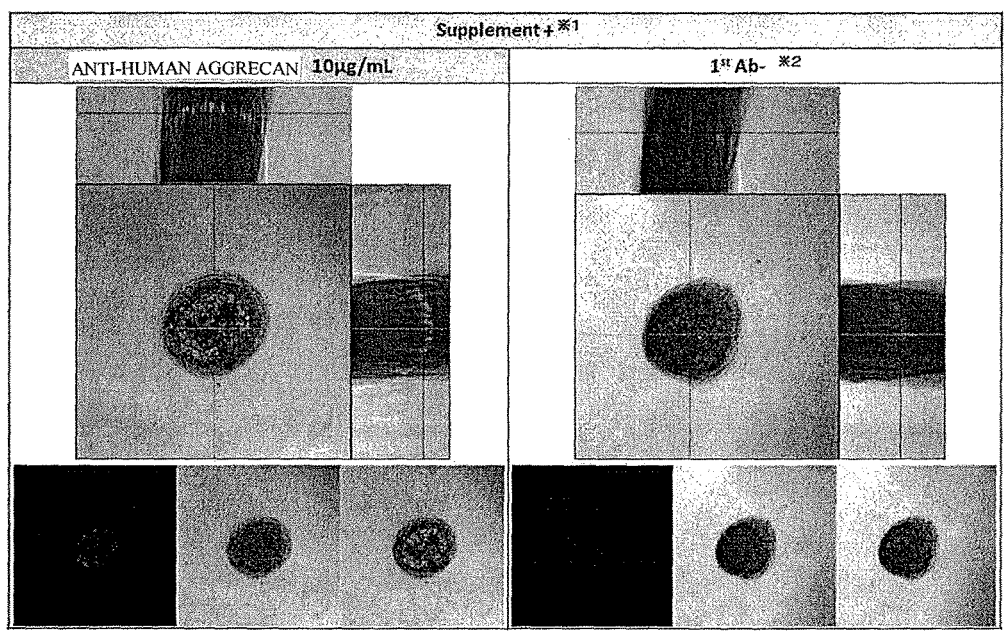
FIG. 12 is a figure showing results of immunostaining tests of hMSCs by using an anti-aggrecan antibody. The hMSCs were cultured in Example 8, and were then subjected to a chondrocyte differentiation inducing test for 4 weeks.

In addition, hMSCs that were cultured in Example 8 and subjected to the osteocyte differentiation test were immunostained with an anti-aggrecan antibody 3 weeks and 4 weeks after the test (see, FIGS. 11 and 12).

As shown in FIGS. 11 and 12, hMSCs subjected to chondrocyte differentiation induction for 3 weeks and 4 weeks showed significant expression of aggrecan, and thus it was confirmed that the chondrocyte differentiation potential was maintained.

With the results of above, it was confirmed that differentiation potential to three directions, that is, to adipocytes, osteocytes, and chondrocytes was maintained in hMSCs that were harvested in Example 8.

The invention claimed is:

1. A somatic stem cell-containing culture liquid, comprising:
   mesenchymal stem cells suspended in a culture liquid, the culture liquid including a dissolved or dispersed material for an undifferentiated state-maintaining culture, wherein
   the dissolved or dispersed material includes crystalline cellulose in the form of nanofibers having an average fiber diameter (D) of 1 nm to 100 nm.

2. The somatic stem cell-containing culture liquid according to claim 1, wherein
   the dissolved or dispersed material for the undifferentiated state-maintaining culture is suspended in the culture liquid at a concentration of 0.0001% (w/v) to 2% (w/v) to a total volume of the somatic stem cell-containing culture liquid, and
   the somatic stem cell-containing culture liquid contains $1.0 \times 10^3$ to $1.0 \times 10^6$ of the mesenchymal stem cells in a unit volume (1 mL).

3. The somatic stem cell-containing culture liquid according to claim 1, further comprising a serum.

4. The somatic stem cell-containing culture liquid according to claim 3, wherein the serum is selected from the group consisting of fetal bovine sera, human sera, horse sera, and chicken sera.

5. The somatic stem cell-containing culture liquid according to claim 3, wherein the serum is contained at a concentration of 0.1% by volume to 50% by volume to a total volume of the somatic stem cell-containing culture liquid.

6. The somatic stem cell-containing culture liquid according to claim 1, further comprising a cellular function regulatory factor.

7. The somatic stem cell-containing culture liquid according to claim 1, wherein a ratio of an average fiber length (L) to the average fiber diameter (D) (L/D) of the nanofibers is 2 to 500.

* * * * *